United States Patent [19]

Porter

[11] Patent Number: 5,676,676

[45] Date of Patent: Oct. 14, 1997

[54] LIGATING CLIP HAVING RAMP-SHAPED VESSEL-CLAMPING MEMBERS

[76] Inventor: Wayne Porter, Rte. 1, Bowie, Tex. 76230

[21] Appl. No.: 521,233

[22] Filed: Aug. 30, 1995

[51] Int. Cl.[6] ................................................ A61B 17/08
[52] U.S. Cl. .............................................. 606/158; 606/151
[58] Field of Search ................................... 606/157, 158, 606/151, 120, 207, 139, 142

[56] References Cited

U.S. PATENT DOCUMENTS

| 4,519,392 | 5/1985 | Lingua | 606/157 |
| 4,835,824 | 6/1989 | Durham et al. | 606/157 |
| 5,188,636 | 2/1993 | Fedotov | 606/157 |
| 5,281,228 | 1/1994 | Wolfson | 606/157 |

Primary Examiner—Michael Buiz
Assistant Examiner—Patrick W. Rasche
Attorney, Agent, or Firm—Dunlap & Codding PC

[57] ABSTRACT

A ligating clip having surfaces with slanted ramp members for clamping a tubular vessel. The ligating clip includes a pair of legs, each of which has a proximal end, a distal end and an inner surface. The proximal ends of the legs are joined to define a hinge. The legs may be forced together onto a tubular vessel such that the inner surfaces of the legs are face-to-face in a closed position. A lock tab protrudes inward from the inner surface near the distal end of one of the legs. A lock slot is provided in the inner surface near the distal end of the other leg. The lock slot receives the lock tab to secure the ligating clip in the closed position. A number of ramp members extend angularly inward from the inner surface of each leg in order to keep the tubular vessel from slipping in the distal direction as the ligating clip is closed.

12 Claims, 2 Drawing Sheets

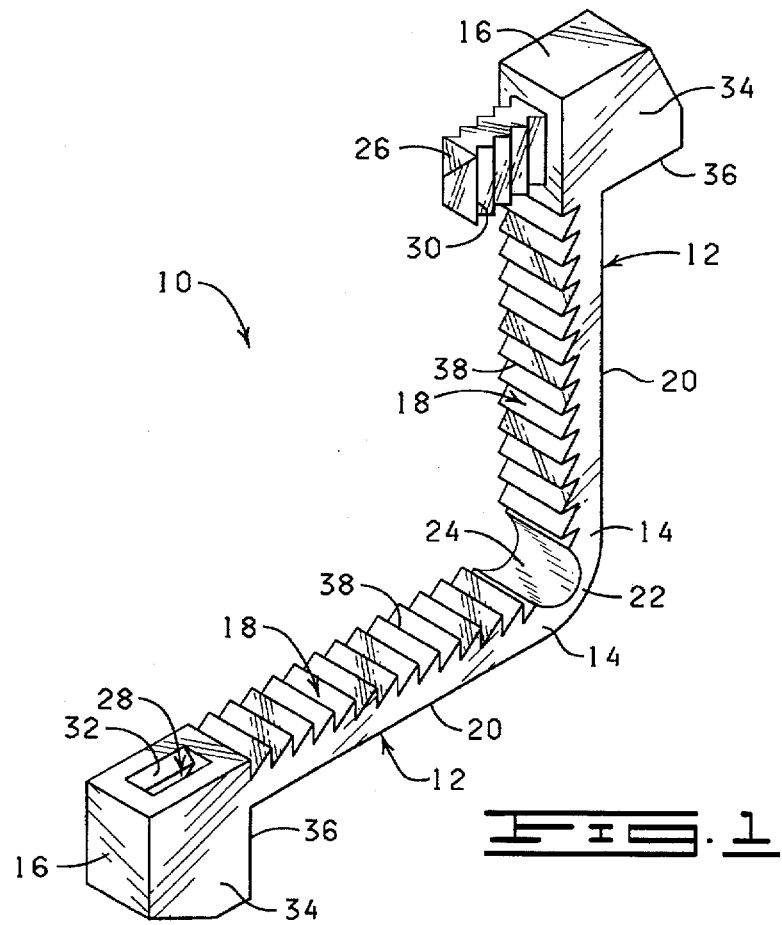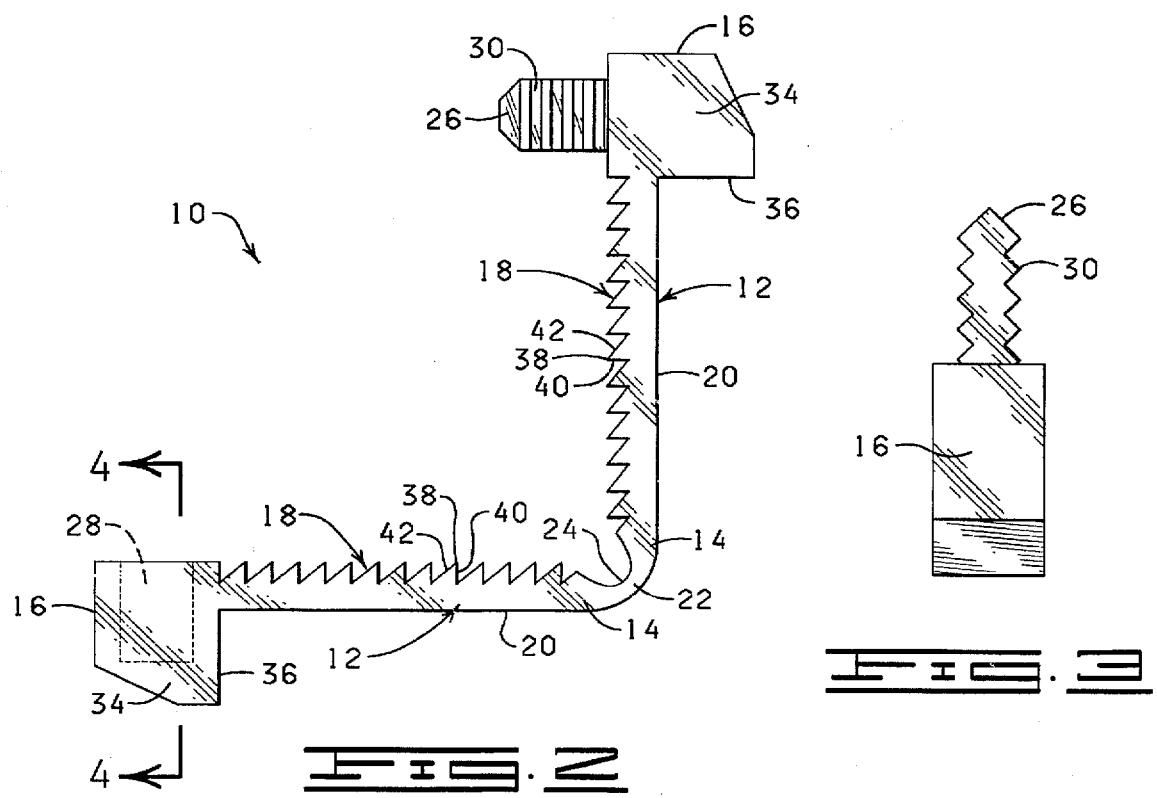

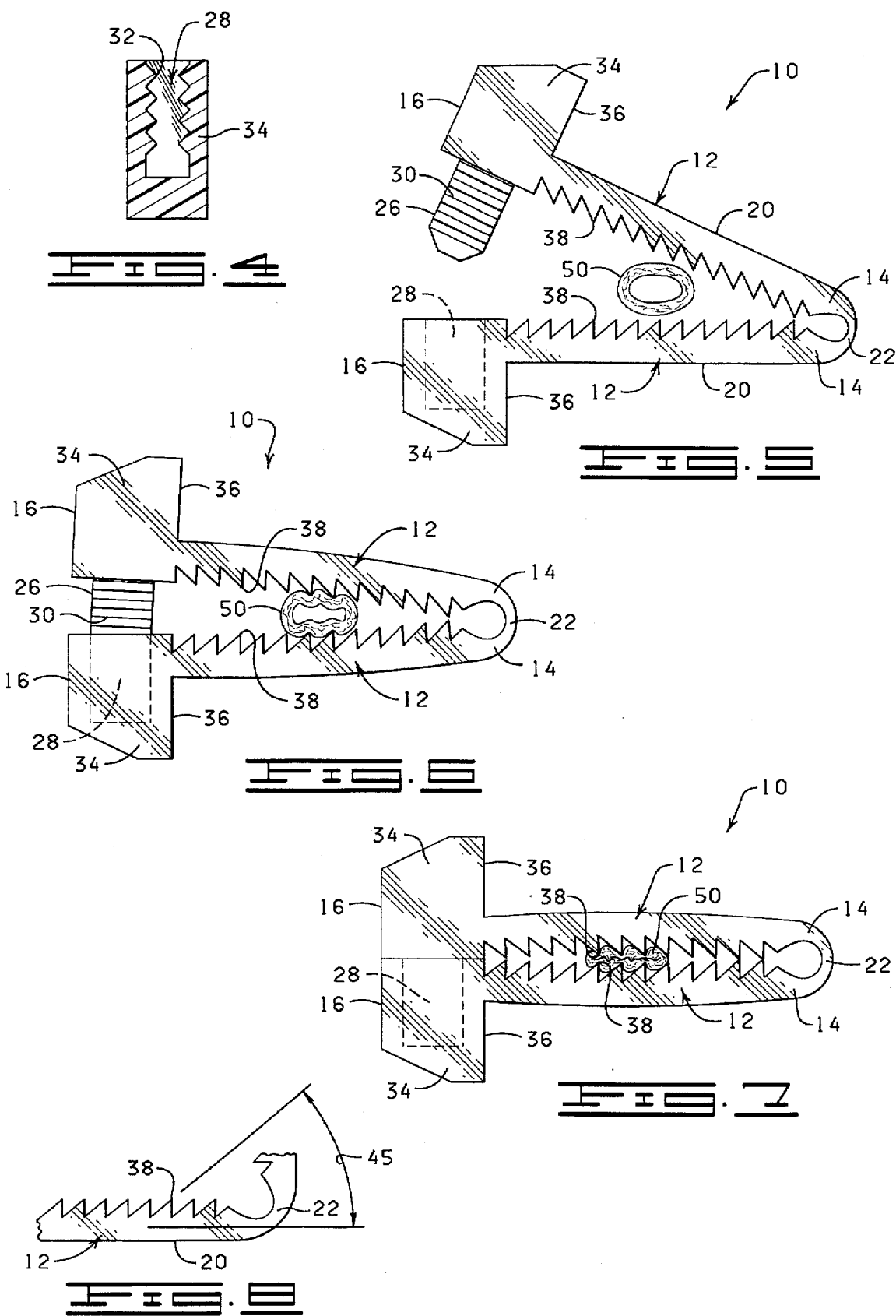

5,676,676

LIGATING CLIP HAVING RAMP-SHAPED VESSEL-CLAMPING MEMBERS

BACKGROUND OF THE INVENTION

1. Field of the Invention

The present invention relates generally to ligating clips, and particularly, but not by way of limitation, to ligating clips for clamping off the vessels of an animal being castrated.

2. Description of Related Art

Various types of ligating clips are known in the art. Most of the conventional clips are surgical or hemostatic clips for use on the vessels of human beings. Such clips have many different designs for the faces which cooperate to close off the vessel.

For example, U.S. Pat. No. 4,449,531 discloses hemostatic clips with flat vessel clamping faces. On the other hand, U.S. Pat. No. 4,346,869 discloses a tube clamp having concave and convex clamping members. U.S. Pat. No. 4,390,019 issued to LeVeen et al. discloses a blood vessel clamp which has a cushion of resilient material on the clamping surfaces.

A clamp for thin-walled tubing is disclosed in U.S. Pat. No. 3,874,042. This particular clamp has at least two spaced longitudinal ridges on one mating member and longitudinal grooves on the second mating member.

U.S. Pat. No. 3,854,482 issued to Laugherty et al. discloses an umbilical cord clamp. This clamp has teeth for gripping a cord on the inner edge portions of its arms. These teeth protrude in a direction which is normal to the arms.

These clips may work well on human subjects, in which case the vessels being ligated can be held securely during application of the clip. However, when used to clamp vessels of animals being castrated, conventional clips are plagued with a common problem: the vessels tend to be pushed out of the clip by the closing action of the clip. This problem is exacerbated by slippery soft tissue and body fluids which accompany the vessels and the task of immobilizing a nervous and impatient animal weighing hundreds of pounds.

SUMMARY OF THE INVENTION

The present invention is a ligating clip which holds the vessel within the clamping surfaces as the clip is closed on the vessel. This "holding in" action compensates for the "pushing out" action caused by the closure of the clip.

A ligating clip constructed in accordance with the present invention includes a pair of legs, wherein each one of the legs has a proximal end, a distal end and a vessel-clamping surface. The proximal ends of the legs are connected to define a hinge.

The distal end of one leg has a lock tab and the distal end of the other leg has a lock slot. When the clip is closed, the lock slot receives the lock tab and secures the clip in the closed position.

The vessel-clamping surfaces of the legs are the surfaces which face one another. Both vessel-clamping surfaces have a plurality of protruding ramp members. Each ramp member is slanted inward toward the hinge of the ligating clip.

One object of the present invention is to provide a ligating clip which is particularly suitable for use in conjunction with the castration of calves and other animals.

Another object of the present invention is to provide a ligating clip which does not have the tendency to push vessels out of the clip as the clip is closed onto the vessels.

Other objects, features and advantages of the present invention are apparent from the following detailed description when read in conjunction with the accompanying drawings and appended claims.

BRIEF DESCRIPTION OF THE DRAWINGS

FIG. 1 is a perspective view of a ligating clip constructed in accordance with the present invention.

FIG. 2 is a side view of the ligating clip of FIG. 1.

FIG. 3 is an end view of the ligating clip leg having the lock tab.

FIG. 4 is a sectional view of the ligating clip taken along the lines 4—4 of FIG. 2.

FIG. 5 is a side view of an open ligating clip with a vessel disposed between the vessel-clamping surfaces of the clip.

FIG. 6 is the same view as FIG. 5, but with the clip partially closed on the vessel.

FIG. 7 is the same view as FIG. 6, but with the clip completely closed and locked onto the vessel.

FIG. 8 is a partly diagrammatical view of a portion of one of the legs to illustrate the angular orientation of the ramp members of the ligating clip.

DETAILED DESCRIPTION OF THE PREFERRED EMBODIMENTS

Referring to the drawings in general, and to FIGS. 1 and 2 in particular, shown therein and designated by the general reference numeral 10 is a ligating clip constructed in accordance with the present invention. The ligating clip 10 includes a pair of legs 12, wherein each one of the legs 12 has a proximal end 14, a distal end 16, an inner surface 18 and an outer surface 20.

The proximal ends 14 of the legs 12 are joined to define a hinge 22. The legs 12 are movable about the hinge 22 between an open position (FIGS. 1, 2 and 5) and a closed position (FIG. 7). A recessed area 24 is provided at the hinge 22 to facilitate the closing of the ligating clip 10.

A lock tab 26 extends inward from the inner surface 18 of one of the legs 12 near the distal end 16 of the leg 12. Near the distal end 16 of the inner surface 18 of the other leg 12, a lock slot 28 is provided for receiving the lock tab 26 when the ligating clip 10 is closed.

The lock tab 26 and lock slot 28 have a plurality of complementary ridges which cooperate to secure the lock tab 26 within the lock slot 28 when the ligating clip 10 is closed. One of the ridges of the lock tab 26 is designated by reference numeral 30 and is generally representative of the ridges on the lock tab 26 (FIGS. 1 and 3). One of the ridges of the lock slot 28 is designated by reference numeral 32 and is generally representative of the ridges on the lock slot 28.

In a preferred embodiment, the ridges 30 are located on opposite sides of the lock tab 26 and the ridges 32 are positioned on opposite sides of the lock slot 28. The other sides of the lock tab 26 and lock slot 28 are substantially flat surfaces. However, a wide variety of locking mechanisms may be employed to secure the ligating clip 10 in the closed position.

It is desirable that an end portion of the lock tab 26 be tapered. With the tapered end, the lock tab 26 guides itself into the lock slot 28 as the ligating clip 10 is closed.

An ear 34 extends outward at the distal end 16 of each leg 12 of the ligating clip 10. Each ear 34 includes a shoulder 36 which generally faces toward the hinge 22 of the ligating clip 10. The shoulders 36 should be shaped such that the mechanism of any suitable ligating tool may push against the shoulders 36 to force closure of the ligating clip 10.

As illustrated by FIGS. 1 and 2, a plurality of ramp members extend inwardly from the inner surface 18 of each leg 12. One of the ramp members for each leg 12 is designated by reference numeral 38 and is generally representative of the ramp members of the ligating clip 10.

Each ramp member 38 has a hinge-facing surface 40 and a ramp surface 42. Typically, the hinge-facing surface 40 of each ramp member 38 is substantially perpendicular to the lengthwise direction of the leg 12 from which the ramp member protrudes. However, it should be appreciated that the hinge-facing surface 40 of each ramp member 38 may slant to define either an acute or an obtuse angle with respect to the lengthwise line of the respective leg 12.

On the other hand, the ramp surface 42 of each ramp member 38 is slanted angularly inward from the lengthwise direction of the leg 12 from which the ramp member protrudes. Thus, the ramp members 38 protrude angularly inward from the inner surface 18 of the respective leg 12 such that each ramp member 38 and the portion of the respective leg 12 extending toward the hinge 22 define an acute angle. As illustrated by FIG. 8, this acute angle 45 is typically between about 30 degrees and 60 degrees and is preferably an angle of approximately 45 degrees.

Each ramp member 38 has a base and tapers to an innermost edge. Thus, the ramp members 38 resemble a saw-toothed arrangement when viewed from the side, as illustrated by FIG. 2.

As best shown in FIG. 1, each ramp member 38 typically extends transversely all the way across the respective leg 12 of the ligating clip 10. However, it should be appreciated that each ramp member 38 may extend across only a part of the respective leg 12.

The ligating clip 10 may be constructed in a wide variety of sizes. It should be appreciated that different sizes of clips may be required for optimal use on different sizes and types of animals. However, for a typical calf, a suitable ligating clip 10 has legs 12 which are about 21 millimeters in length and 2.5 millimeters in width. A leg 12 with these dimensions typically has 8 to 16 ramp members 38 which are from 0.5 to 1.0 millimeters in length.

The ligating clip 10 may be constructed of any suitable metallic or nonmetallic material which is known in the art. Further, the ligating clip 10 may be made of an absorbable or a non-absorbable substance.

For non-absorbable materials, the ligating clip 10 may be made of nylon, polypropylene or the like. For making a clip which is absorbable, the ligating clip 10 may be constructed of homopolymers and copolymers of glycolide and lactide, p-diaxanone or any other absorbable polymers known in the art.

Operation

The application of the ligating clip 10 to a vessel is best understood with reference to FIGS. 5 through 7. As shown in FIG. 5, the open ligating clip 10 is positioned with the legs 12 on opposing sides of a tubular structure or tubular vessel 50. The longitudinal axis of the vessel 50 and the legs 12 of the ligating clip 10 are generally perpendicular to one another. The tubular vessel 50 is situated in an intermediate area between the ramp members 38 of the two legs 12.

In FIG. 5, the ligating clip 10 is partially closed on the tubular vessel 50. As the ligating clip 10 is closed, the angular orientation of the ramp members 38 applies a gripping force toward the hinge 22 on the vessel 50 and offsets the tendency of the vessel 50, made slippery by soft tissue and body fluids, to slide toward the distal ends 16 of the legs 12. At approximately this point, the lock tab 26 begins to enter the lock slot 28 and the ridges 30 and 32 of the lock tab 26 and lock slot 28, respectively, begin to interlock.

As illustrated by FIG. 7, the ligating clip 10 finally is closed completely on the tubular vessel 50 to constrict flow through the vessel 50. The ridges 30 and 32 of the lock tab 26 and the lock slot 28 are fully interlocked to secure the ligating clip 10 on the vessel 50.

Changes may be made in the combinations, operations and arrangements of the various parts and elements described herein without departing from the spirit and scope of the invention as defined in the following claims.

What is claimed is:

1. A ligating clip, comprising:

a pair of legs, each one of the legs having a proximal end, a distal end, an inner surface extending between the proximal and distal ends thereof, and a plurality of ramp members extending from the inner surface of each of the legs, each of the ramp members angled toward the proximal end of their respective leg;

hinge means for joining the proximal ends of the legs such that the legs are movable from an open position wherein the legs are spread apart to receive a vessel therebetween to a closed position wherein the legs are substantially together so that the ramp members of the legs grippingly clamp the vessel positioned therebetween so as to constrict fluid flow through the vessel, the ramp members cooperating to apply a force on the vessel toward the hinge as the legs are moved from the open position to the closed position to retain the vessel between the legs and resist movement of the vessel toward the distal ends of the legs; and means for securing the legs in the closed position.

2. The ligating clip of claim 1 wherein the ramp members are arranged on the legs so that the edges of opposing ramp members are substantially aligned when the legs are in the closed position.

3. The ligating clip of claim 1 wherein the ligating clip is constructed of an absorbable polymer.

4. The ligating clip of claim 1 wherein each of the ramp members extends substantially across the inner surface of the corresponding leg.

5. The ligating clip of claim 1 wherein the ligating clip is constructed of a substance selected from the group consisting of nylon, polypropylene, lactide homopolymer, lactide copolymer, glycolide homopolymer, glycolide copolymer and p-diaxanone.

6. A ligating clip for controlling hemorrhaging when castrating an animal, comprising:

a pair of legs, each one of the legs having a proximal end, a distal end, an inner surface extending between the proximal and distal ends thereof, and a plurality of ramp members extending from the inner surface of each of the legs, each of the ramp members having a first surface generally facing the proximal end of the leg and a second surface generally facing the distal end of the leg, the length of the second surface of each ramp member being greater than the length of the first surface of each corresponding ramp member such that each of the ramp members is angled toward the proximal end of the leg;

hinge means for joining the proximal ends of the legs such that the legs are movable from an open position wherein the legs are spread apart to receive a vessel therebetween to a closed position wherein the legs are substantially together so that the ramp members of the legs grippingly clamp the vessel positioned therebetween so as to constrict fluid flow through the vessel, the ramp members cooperating to apply a force on the vessel toward the hinge as the legs are moved from the open position to the closed position to retain the vessel between the legs and resist movement of the vessel toward the distal ends of the legs; and means for securing the legs in the closed position.

7. The ligating clip of claim 6 wherein the ramp members are arranged on the legs so that the edges of opposing ramp members are substantially aligned when the legs are in the closed position.

8. The ligating clip of claim 6 wherein the angle between the first surface of each of the ramp members and the inner surface of the leg from which the ramp members extend is about 90 degrees.

9. The ligating clip of claim 8 wherein the angle between the second tapered surface of each of the ramp members and the inner surface of the leg from which the ramp members extend is between about 30 and 60 degrees.

10. The ligating clip of claim 6 wherein the ligating clip is constructed of an absorbable polymer.

11. The ligating clip of claim 6 wherein each of the ramp members extends substantially across the inner surface of the corresponding leg.

12. The ligating clip of claim 6 wherein the ligating clip is constructed of a substance selected from the group consisting of nylon, polypropylene, lactide homopolymer, lactide copolymer, glycolide homopolymer, glycolide copolymer and p-diaxanone.

* * * * *